United States Patent [19]

Sawai et al.

[11] Patent Number: 5,532,272
[45] Date of Patent: Jul. 2, 1996

[54] 3-OXYGERMYLPROPIONIC ACID POLYMER, PHARMACEUTICAL COMPOSITION CONTAINING SAME AND METHOD OF PREVENTING AND/OR CURING SYMPTOMS OF IMMUNE DISEASES USING SAME

[75] Inventors: Kiichi Sawai; Takahiko Mitani; Naohisa Ninomiya; Yoshirou Ishiwata, all of Nagoya, Japan

[73] Assignee: Sanwa Kagaku Kenkyusho Co., Ltd., Nagoya, Japan

[21] Appl. No.: 246,141

[22] Filed: May 20, 1994

[51] Int. Cl.⁶ .............................. A61K 31/28; C07F 7/30
[52] U.S. Cl. ................................................ 514/492; 556/93
[58] Field of Search ................................ 556/93; 514/492

[56] References Cited

PUBLICATIONS

The Washington Post, Feb. 1995.
AIDS 1994, vol. 8 (suppl 1), pp. 561–569 (1994).
Steve Sternberg, Bio World Today, vol. 6, No. 22, pp. 1–5 (1995).

*Primary Examiner*—Porfirio Nazario-Gonzales
*Attorney, Agent, or Firm*—Sughrue, Mion, Zinn, Macpeak & Seas

[57] ABSTRACT

A novel, eight structural polymer of 2-oxygermylpropionic acid having an empirical formula of $C_6H_{10}Ge_2O_7$, a minimum constitutional unit of $(O_{1/2})_3GeCH_2CH_2COOH$ and the following stereostructure:

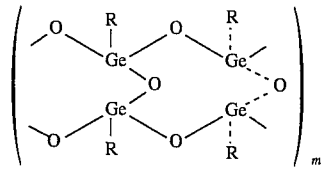

wherein R stands for —$CH_2CH_2COOH$ and m is an integer of 137±84. A pharmaceutical composition containing the novel polymer is useful for preventing symptoms of an immune disease such as hepatitis or for curing such a disease.

4 Claims, No Drawings

3-OXYGERMYLPROPIONIC ACID POLYMER, PHARMACEUTICAL COMPOSITION CONTAINING SAME AND METHOD OF PREVENTING AND/OR CURING SYMPTOMS OF IMMUNE DISEASES USING SAME

BACKGROUND OF THE INVENTION

1. Field of the Invention

This invention relates to a new, eight structural polymer of 2-oxygermylpropionic acid and to a pharmaceutical composition containing same. The present invention is also directed to a method of preventing the occurrence of symptoms of immune diseases or curing such diseases.

2. Description of the Prior Art

3-Oxygermylpropionic acid which undergoes polymerization in a complicated manner is useful for various applications. In particular, because of the specific pharmacological activities, 3-oxygermylpropionic acid compounds have now attracted attention of many researchers. Japanese Examined Patent Publication No. 57-53800 discloses antiviral activities of such compounds.

Carboxyethylgermanium sesquioxide, generally called Ge132, is known to have a twelve-membered ring structure (J. Am. Chem. Soc., 98 (25), 8287 ( 1976)).

The known organogermanium compounds, however, have a problem that it is difficult to synthesize the compounds with good reproducibility. Thus, the pharmacological activities of the known compounds vary from lot to lot. Additionally, the known compounds encounter a problem because the activities are lowered during dispensing.

The present inventors have proposed effective stabilizing agents for 3-oxygermylpropionic acid (Japanese Unexamined Patent Application No. 61-65819) and also found that sugar serves to enhance the pharmacological activities of the acid (Japanese Unexamined Patent Application No. 60-190714).

SUMMARY OF THE INVENTION

It is an object of the present invention to provide a novel organogermanium compound which exhibits high pharmacological activities.

Another object of the present invention is to provide an organogermanium compound of the above-mentioned type whose activities are independent from the manner or conditions in which the compound has been synthesized.

It is a special object of the present invention to provide a pharmaceutical composition which is useful for preventing the occurrence of symptoms of immune diseases, especially hepatitis, nephritis and AIDS, or curing such diseases.

It is a further object of the present invention to provide a method of preventing and/or curing symptoms of immune diseases.

In accomplishing the foregoing objects, there is provided in accordance with one aspect of the present invention an organogermanium compound having an empirical formula of $C_6H_{10}Ge_2O_7$, a minimum constitutional unit of $(O_{1/2})_3GeCH_2CH_2COOH$ and the following stereostructure:

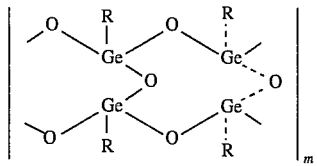

wherein R stands for —$CH_2CH_2COOH$ and m is an integer of 137±84.

The number "m" represents a weight average polymerization degree calculated on the basis of the weight average molecular weight of propagermanium propyl ester and is 137 on average with a standard deviation of ±3σ.

In another aspect, the present invention provides a pharmaceutical composition containing the above organogermanium compound.

In a further aspect, the present invention provides a method of preventing and/or curing symptoms of an immune diseases of a subject, which includes administering a pharmacologically effective amount of a composition containing the above organogermanium compound to the subject.

The present inventors have found that compounds expressed by the formula $[(O_{1/2})_3GeCH_2CH_2 COOH]_n$ include three groups with different stereostructures. One of the three groups includes the compound of the present invention and shows higher activities than the other two groups.

The chemical and physical properties of the compound according to the present invention (hereinafter referred to as OGP-8) are as summarized in Tables 1 and 2. Table 1 shows the results of the molecular weight measurement by the light scattering method while Table 2 shows the lattice constant determined by the powder X-ray diffraction method.

TABLE 1

|  | OGP-8 Propyl Ester | OGP-8 (equivalent value) |
|---|---|---|
| Weight Average Molecular Weight (Mw) | | |
| Average (X) | $1.16 \times 10^5$ | $9.29 \times 10^4$ |
| Standard deviation 3σ | $\pm 0.71 \times 10^5$ | $\pm 5.72 \times 10^4$ |
| Molecular Formula* | $(C_6H_{11}GeO_{3.5})_n$ | $(C_3H_5GeO_{3.5})_n$ |
| Weight Average Polymerization Degree (n)* | 548 ± 337 | 548 ± 337 |

*n is an integer determined provided that the minimum constitutional unit of OGP-8 is $(O_{1/2})_3GeCH_2CH_2COOH$

TABLE 2

| Chemical formula *1 | $C_3H_5GeO_{3.5}$ |
|---|---|
| Formula weight *1 | 169.66 |
| Crystal class | monoclinic |
| Space group | — |
| Unit cell parameters | |
| a (Å) | 13.35 (1) |
| b (Å) | 5.03 (1) |
| c (Å) | 7.55 (2) |
| β(deg.) | 94.3 (2) |
| vol (Å³) | 505.4 *2 |
| z | 4 *3 |
| Density (gcm⁻³) | 2.23 *4 |

*1: indicated provided that the minimum constitutional unit of OGP-8 is $(O_{1/2})_3GeCH_2CH_2COOH$
*2: calculated on the basis of the lattice constants
*3: calculated on the basis of lattice constants and the measured density
*4: measured by the floating method Other objects, features and advantages of the present invention will become apparent from the detailed description of the preferred embodiments of the invention to follow.

DETAILED DESCRIPTION OF THE PREFERRED EMBODIMENTS OF THE INVENTION

The pharmaceutical composition containing OGP-8 may be any desired form such as a tablet or a capsule. It is preferred that OGP-8 be used in conjunction with a carrier for stabilizing the phamacological activity thereof. Examples of suitable carriers include sugar such as lactose, sucrose and dextran; modified cellulose such as hydroxypropylcellulose; and naturally occurring polymers such as albumin. The carrier is generally used in an amount of 0.001 to 1,000 parts by weight per part by weight of OGP-8. If desired, the composition may additionally contain a drug which is generally used for curing immune diseases. Illustrative of suitable drugs are antiviral agents for viral hepatitis, antiallergic agents for allergic diseases and anticancerous agents for cancer. By using such a drug in combination with OGP-8, the toxicity of the drug may be relieved while maintaining the curative activities high. Depending upon the type of the drug, the pharmaceutical composition may be formulated into an enteril form.

The composition of the present invention is generally administered to humans at a dose of 1–1,500 mg/day, though the dose is variable depending upon the type or form of the composition, the age of patients, etc. In the case of adults (weighing 50 kg), for example, the dose is preferably 10–150 mg/day.

The following examples will further illustrate the present invention.

Example 1

Preparation of OGP-8:

In 2 liters of ethanol were dissolved 252 g (1 mole) of 3-trichlorogermylpropionic acid to obtain a solution, to which 1.5 liters of water were slowly added while maintaining the mixture at 20° C. It took several hours to completely add the water. The mixture was allowed to stand for 24 hours and the precipitates were then separated by filtration, washed with acetone and dried under vacuum, thereby to obtain OGP-8 with a yield of 90%.

Example 2

Composition in the form of Tablet:

Using ethanol as a wetting agent, 2 parts by weight of OGP-8 and 1 part by weight of hydroxypropylcellulose were kneaded together. The kneaded blend was then dried at 50° C. or less to obtain a powdery or granular mixture. This mixture was blended with the following ingredients and the blend was tableted in a conventional manner.

| | |
|---|---|
| Mixture containing OGP-8 | 10.0 mg |
| Lactose | 159.2 mg |
| Carboxymethylcellulose (Na) | 8.0 mg |
| Soft silica | 2.0 mg |
| Magnesium stearate | 1.8 mg |
| | 180.0 mg/tablet |

Example 3

Pharmacological Test:

Seven-age BALB/c mice were each subcutaneously transplanted with $2 \times 10^6$ Sarcoma-180 cells. Nine days after the transplantation, OGP-8 was daily per os administered to the mice at doses of 0.3, 1, 3, 10 and 30 mg/kg/day for five days. The next day after the completion of the medication, each mouse was sensitized with $2 \times 10^8$ sheep red blood corpuscles (SRBC) by intravenous injection. Four days after g the sensitization, the spleen of each mouse was enucleated to measure the amount of SRBC IgM-PFC in the cell.

For the purpose of comparison, the above procedure was repeated in the same manner as described except that Gel32 (carboxyethylgermanium sesquioxide) was used in lieu of OGP-8.

The results were as summarized in Table 3. As seen from Table 3, a dosage of 0.3 mg/kg of OGP-8 can significantly recover the ability of the cancer-bearing mice to produce the antibody. The PFC number becomes maximum with a dosage of 1–3 mg/kg. Significant antibody production-enhancing effect is obtainable with a dosage of up to 10 mg/kg. In contrast, with G132, significant effect is obtainable only when the dosage is 30 mg/kg. Thus, it is appreciated that OGP-8 is effective in increasing the antibody producing ability of the animals which has been lowered due to cancer and that OGP-8 is about 100 times as effective as Gel32.

TABLE 3

| | Dosage (mg/kg) | IgM-PFC Number/ $10^6$ Spleen Cell |
|---|---|---|
| Normal Mice Group (control) | — | 1,613 ± 107*** |
| Cancer Mice Group (control) | — | 740 ± 40 |
| OGP-8 Dosed Mice Group | 0.3 | 984 ± 61** |
| | 1 | 1,269 ± 112*** |
| | 3 | 1,258 ± 82*** |
| | 10 | 1,004 ± 102* |
| | 30 | 909 ± 64* |
| Ge132-Dosed Mice Group | 0.3 | 770 ± 77 |
| | 1 | 779 ± 63 |
| | 3 | 805 ± 97 |
| | 10 | 826 ± 60 |
| | 30 | 995 ± 69** |

IgM-PFC number is an average in 7 mice ± standard deviation.
Significance:
** $p < 0.01$,
*** $p < 0.001$

Example 4

Pharmacological Test:

The action of OGP-8 on preventing nephritis was examined. Given amounts of OGP-8 were per os administered to MRL/1 masculine mice once a day for 12 weeks. In the meantime, urinary protein was measured once a week, wherein urinary protein levels exceeding 100 mg/dl were taken as positive. Examination was then made on how many animals became positive at respective week-ages. Further, blood-urinary nitrogen levels were determined on the day following the final administration to make serological/physiological and pathological estimations of the action of OGP-8 on nephritis.

The tests pertaining to the urinary protein levels and blood-urinary nitrogen levels revealed that OGP-8 is effective for inhibiting the occurrence of symptoms of nephritis and that dosage of 3 mg/kg/day gives the best results. No nephritis inhibiting effect was obtained in the case of indomethacin as a comparative.

In general, MRL/1 mice develop major symptoms of membranoproliferative glomerulonephritis. In the control group, 57% of glomeruli became morbid, but only 23–34% does in the groups medicated with OGP-8. Thus, it is found that OGP-8 produces an inhibitory action on the spontaneous development of nephritis in MRL/1 mice. In the case of the groups dosed with indomethacin, nearly the same results as in the case of the control groups were obtained.

Altogether, OGP-8 is efficacious against the development of spontaneous nephritis in MRL/1 mice from the standpoints of serology/physiology and pathology. These effects attained by OGP-8 are not obtainable with conventional non-steroid antiinflammatory agents.

Example 5

Clinical Test:

The efficacy of OGP-8 against Type B chronic hepatitis was examined. Patients positive to HBe antigens and having Type B chronic hepatitis were each dosed with 10 mg of OGP-8 after each meal three times a day in principle over 16 weeks. Each patient was diagnosed for the over-all judgement by the physician in charge. The results are summarized in Table 4. As will be seen from the rate of amelioration reported in Table 4, OGP-8 is effective for inhibiting Type B hepatitis.

TABLE 4

| Evaluation* | A | B | C | D | E | F | G | Total Percentage A–G | A–B | A–C |
|---|---|---|---|---|---|---|---|---|---|---|
| Case Number | 10 | 25 | 25 | 28 | 7 | 1 | 0 | 96 | 36.5 | 62.5 |

Evaulation:
A: Extremely ameliorated
B: Fairly ameliorated
C: Slightly ameliorated
D: No change
E: Slightly aggravated
F: Fairly aggravated
G: Extremely aggravated Example 6

Clinical Test:

The efficacy of OGP-8 against Type C chronic hepatitis was examined. Patients positive to HBe antigens and having Type C chronic hepatitis were each dosed with 20 mg of OGP-8 after each meal three times a day in principle over 24 weeks. Each patient was diagnosed for the over-all judgement by the physician in charge. The results are summarized in Table 5. As will be seen from the rate of amelioration reported in Table 5, OGP-8 is effective for inhibiting Type C hepatitis.

TABLE 5

| Evaluation* | A | B | C | D | E | F | G | Total Percentage A–G | A–B | A–C |
|---|---|---|---|---|---|---|---|---|---|---|
| Case Number | 1 | 5 | 5 | 7 | 0 | 0 | 20 | 30.0 | 55.0 |

Evaulation:
A: Extremely ameliorated
B: Fairly ameliorated
C: Slightly ameliorated
D: No change
E: Slightly aggravated
F: Fairly aggravated
G: Extremely aggravated Example 7

Clinical Test:

The efficacy of OGP-8 against symptoms of AIDS have been examined. Twenty patients infected with AIDS have been each dosed with 10 mg of OGP-8 after each meal three times a day in principle over 1 year, while being diagnosed by the physician in charge. Up to now, no symptoms of AIDS have occurred.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. An organogermanium compound having an empirical formula of $C_6H_{10}Ge_2O_7$, a minimum constitutional unit of $(O_{1/2})_3GeCH_2CH_2COOH$ and the following stereostructure:

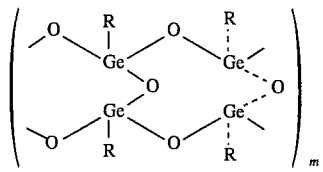

wherein R stands for —$CH_2CH_2COOH$ and m is an integer of 137±84.

2. A composition of matter, comprising an organogermanium compound according to claim 1, and further comprising a carrier.

3. A composition as claimed in claim 2, wherein said carrier is a member selected from the group consisting of lactose, sucrose, dextran, hydroxypropylcellulose and albumin.

4. A composition as claimed in claim 2, further comprising a drug selected from the group consisting of antiviral agents, antiallergic agents and anticancerous agents.

* * * * *